United States Patent
Andrews et al.

(10) Patent No.: US 6,482,178 B1
(45) Date of Patent: Nov. 19, 2002

(54) LOCALIZATION DEVICE WITH ANCHORING BARBS

(75) Inventors: Marvin O. Andrews; Frank J. Fischer, Jr., both of Bloomington; John H. Ward, Spencer, all of IN (US)

(73) Assignee: Cook Urological Incorporated, Spencer, IN (US)

( * ) Notice: Subject to any disclaimer, the term of this patent is extended or adjusted under 35 U.S.C. 154(b) by 0 days.

(21) Appl. No.: 09/566,373

(22) Filed: May 8, 2000

Related U.S. Application Data

(60) Provisional application No. 60/135,233, filed on May 21, 1999.

(51) Int. Cl.[7] ............................................. A61M 5/178
(52) U.S. Cl. ................ 604/164.01; 604/104; 604/106; 604/107; 606/198
(58) Field of Search ................ 64/104, 105, 106, 64/107, 108, 109, 95.04, 95.05, 158, 159, 164.01; 606/198

(56) References Cited

U.S. PATENT DOCUMENTS

| | | | | |
|---|---|---|---|---|
| 4,936,823 A | * | 6/1990 | Colvin et al. ............... | 604/107 |
| 5,256,146 A | * | 10/1993 | Ensminger et al. .......... | 604/104 |
| 5,267,960 A | * | 12/1993 | Hayman et al. ............. | 604/106 |
| 5,312,360 A | * | 5/1994 | Behl .......................... | 604/106 |
| 5,358,496 A | * | 10/1994 | Ortiz et al. .................. | 606/198 |
| 5,620,458 A | * | 4/1997 | Green et al. ................. | 604/104 |
| 5,830,171 A | * | 11/1998 | Wallace ....................... | 604/104 |
| 5,885,258 A | * | 3/1999 | Sachdeva et al. ........... | 604/107 |
| 5,928,266 A | * | 7/1999 | Kontos ........................ | 604/106 |
| 6,027,518 A | * | 2/2000 | Gaber ......................... | 604/105 |
| 6,071,263 A | * | 6/2000 | Kirkman ...................... | 604/104 |
| 6,280,413 B1 | * | 8/2001 | Clark et al. .................. | 604/104 |
| 6,328,727 B1 | * | 12/2001 | Frazier et al. ............... | 604/107 |

* cited by examiner

Primary Examiner—Teresa Walberg
Assistant Examiner—Fadi H. Dahbour
(74) Attorney, Agent, or Firm—James B. Hunt

(57) ABSTRACT

A localization device (10) comprising an outer needle cannula (11), an optional inner sleeve cannula (13) and an anchor stylet comprising a plurality of preformed superelastic alloy wires (12). Once the distal portions (14) of the wires (12) are deployed from the ends of the sleeve and needle cannulae, they function as curved barbs (15) projecting outward to anchor the device into tissue, an organ, or a foreign body. A slidable locking member (18), such as a pin vise, can be included over the outer needle cannula for securing the localization device against a template.

19 Claims, 3 Drawing Sheets

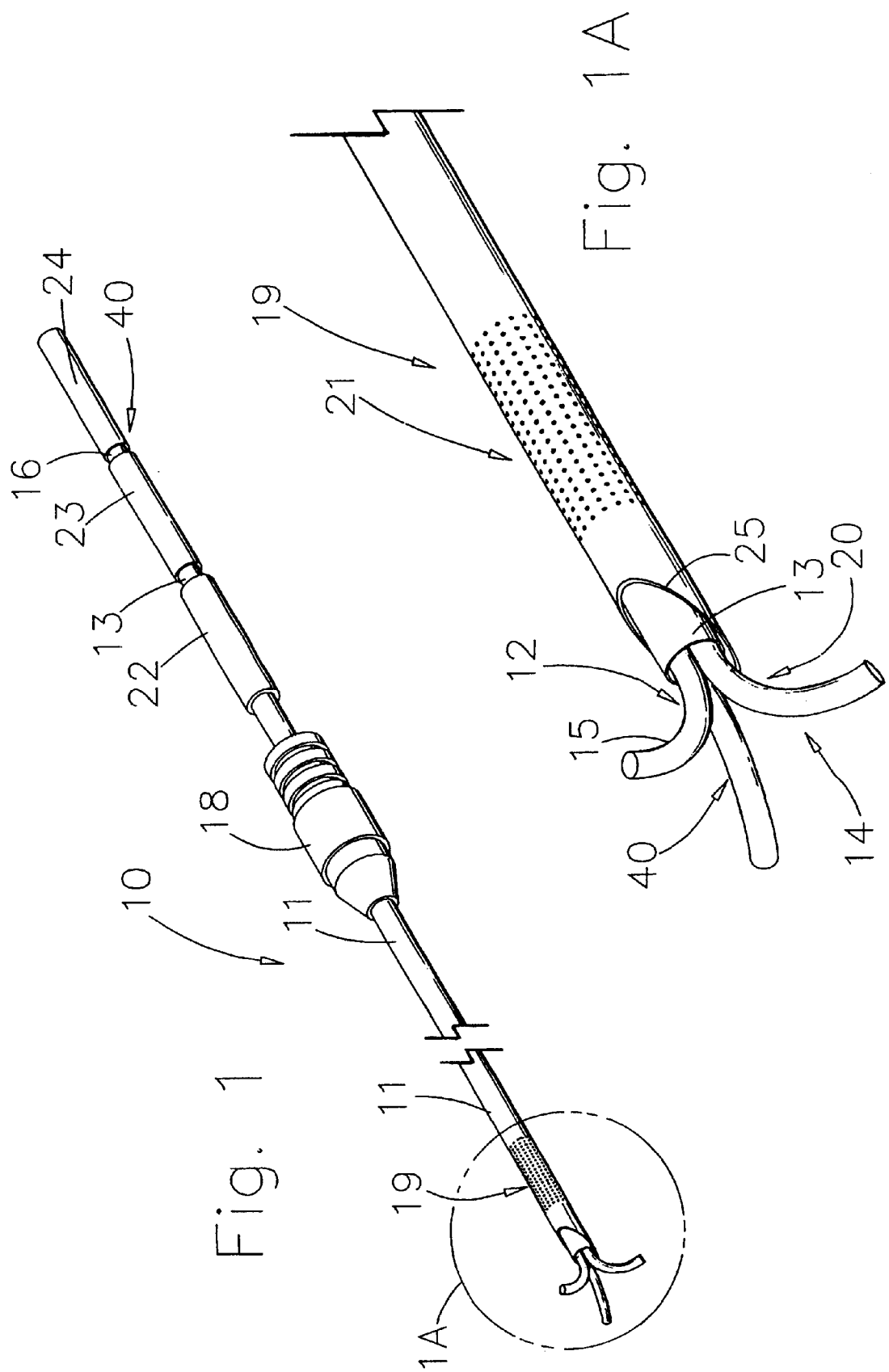

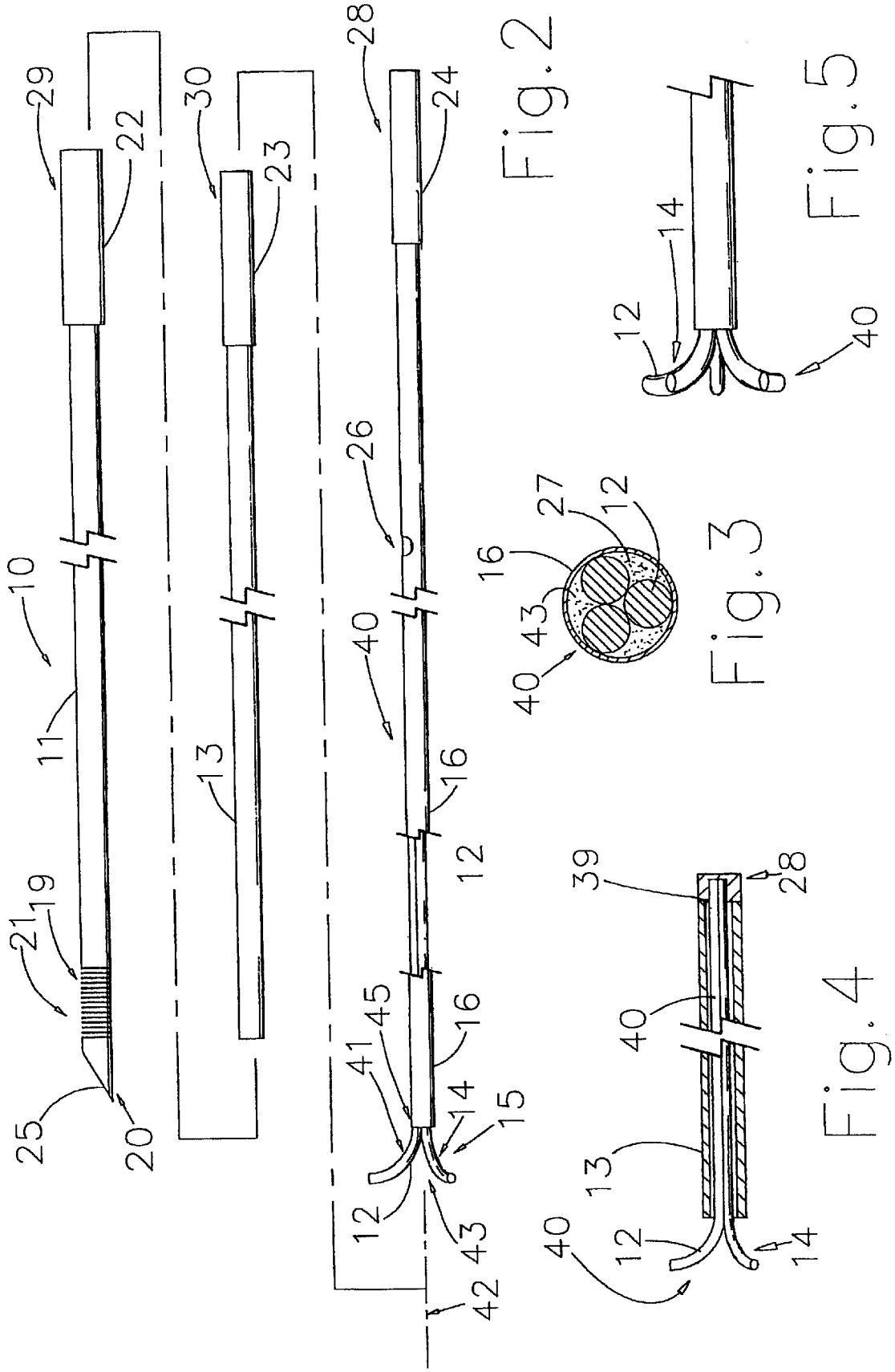

LOCALIZATION DEVICE WITH ANCHORING BARBS

TECHNICAL FIELD

This application claims priority of Provisional Patent Application No. 60/135,233 filed May 21, 1999. This invention relates generally to medical devices, more particularly to minimally invasive localization devices.

BACKGROUND OF THE INVENTION

Localization devices are frequently used in the treatment of tumors to guide treatment to a specific location under fluoroscopy or ultrasound. These devices can be manipulated to engage tissue at the target site via one or more barbs, tines, or other structures to prevent dislodgement or to stabilize the region be treated. During a procedure, there often is a tendency for an organ or other anatomical body to shift as it is being manipulated. Certain procedures optimally require stabilizing the position of the target structure such that precise placement of treatment can occur. For example, in brachytherapy of the prostate, interstitial anchoring devices immobilize the prostate at a fixed distance from a template to allow a brachytherapy needle to penetrate to a known depth for the placement of the radioactive seed. In other applications, anchoring of the target tissue or structure is followed by treatment to same site. The usual practice is for a separate surgical instrument to be guided to the site marked by the localization device. Placement of the second device usually requires a second entry site and increases the duration that the patient is under fluoroscopy.

SUMMARY OF THE INVENTION

The foregoing problems are solved and a technical advance is achieved in an illustrative embodiment of a localization device comprising an outer needle cannula, optionally with a sharp beveled tip, an inner sleeve cannula and an anchor stylet comprising a plurality of preformed superelastic alloy wires that once deployed from the end sleeve and needle cannulae, function as curved barbs projecting outward to anchor the device into tissue, an organ, or a foreign body. The combination of the anchoring wires and sleeve cannula can be removed from the outer needle cannula so that medicants or other materials can be infused at the anatomical site through the needle cannula. If desired, the sleeve cannula and anchoring wires can be easily reintroduced into the needle cannula. Without the sleeve cannula to recompress the anchoring wires for reloading, it would be very difficult to load the anchor stylet with its outwardly-projecting barbs into the needle cannula. In one embodiment, a smaller inner cannula is used to secure the anchoring wires together and facilitate axial movement of the anchor stylet within the sleeve cannula. Possible uses of the localization device include positioning the anchor at a target site and removing the outer needle cannula over the anchor stylet and sleeve cannula. A dilator and sheath can then be placed over the anchor such that a catheter, or other device (e.g., a cryoprobe) can been introduced to the desired location, usually following removal of the anchor stylet and sleeve cannula.

In another embodiment of the present invention, a slidable collet or other locking member, such as a pin vise, can be included over the outer needle cannula for securing the anchoring device against a template such as the type used in a brachytherapy or hyperthermia treatment procedure. The locking member can made to be removable from the proximal end to permit advancement of another device over the needle.

In another aspect of the invention, the surface of the outer needle cannula about the distal end can be made to be echogenic for visibility under ultrasound. Additionally, the radiopacity of the device can be enhanced by the addition of a well-known, biocompatible radiopaque material such as tantalum, platinum, gold, etc., to one or more device components.

BRIEF DESCRIPTION OF THE DRAWINGS

Embodiments of the invention will now be described by way of example with reference to the accompanying drawings, in which:

FIG. 1 depicts a pictorial view of a localization device of the present invention;

FIG. 1A is an enlarged view taken at line 1 A of FIG. 1 to illustrate the distal end of the localization device;

FIG. 2 depicts side views of the disassembled major components of the device of FIG. 1;

FIG. 3 depicts a cross-sectional view taken along line 3—3 of FIG. 2;

FIG. 4 depicts a partially-sectional, enlarged side view of an alternative embodiment of FIG. 1;

FIG. 5 depicts a side view of a second alternative embodiment of FIG. 1;

DETAILED DESCRIPTION

Figure 6:
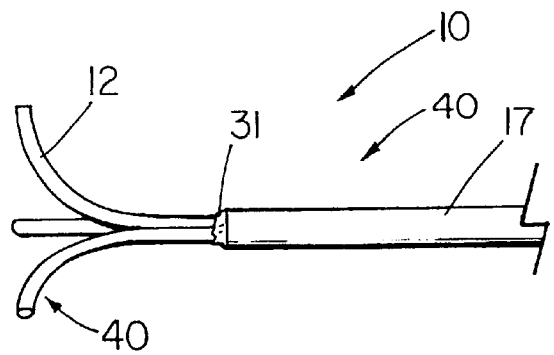
FIG. 6 depicts a side view of a third alternative embodiment of FIG. 1.

An anchoring device 10 of the present invention is depicted in FIGS. 1–3, comprising three major components: an outer needle cannula 11, a cannula sleeve 13, and an anchor stylet 40, the latter being mainly comprised of a plurality of anchoring wires 12. Anchor stylet 40, as shown in FIG. 2, comprises three anchoring wires 12, preferably comprised of a superelastic alloy such as nitinol (NiTi). In the illustrative embodiment, the anchoring wires 12 extend the length of the anchor stylet 40. The distal portion 14 of each anchoring wire 12 is formed into a distal curve 41 that extends laterally from the longitudinal axis 42 of the device 10 (about 2–3 mm in the illustrative embodiment) to form a barb 15 that is capable of positively engaging tissue and anchoring the device 10 therein. As defined herein, barb 15 includes any terminal shape capable of permitting the distal portion 14 of the anchoring wires 12 to remain secured within tissue and resist countertractional force, and includes, but is not limited to, hooks, tines, forks, helixes, and other structures. In the embodiment of FIG. 2, the anchor stylet 40 further comprises an anchoring wire holder 16 comprising a cannula or sleeve that encloses and secures the anchoring wires 12 while providing a low friction surface to facilitate longitudinal movement of the anchor stylet 40 within the coaxial sleeve cannula 13. Sleeve cannula 13 serves as a restraint on the barbs 15, forcing them into a substantially straightened configuration to permit the anchor stylet 40 with sleeve cannula 13 to be loaded or reloaded into the outer needle cannula 11. As shown in FIG. 3, the anchoring wires 12 can be fixedly secured within the lumen 43 of the anchoring wire holder 16 with an adhesive 27 such as LOCTITE™ 4014 cement (Loctite Corporation, Rocky Hill, Conn.). To permit the cement to reach areas along the length of wire holder 16, a series of notches 26 can be made, as shown in FIG. 2, through which the cement can be injected. In the illustrative embodiment, notches 26 are placed at 6 mm and 9–10 cm from proximal end 28, and 3 cm from the distal end 45 of the cannula 16 (the latter two notches not shown). Alternate methods of securing the anchoring wires in the anchoring wire holder 16 include, but are not limited to, crimping, welding, banding, or wrapping. Fixing the anchoring wires 12 within the anchoring wire holder 16 allows the barbs 15 to be maintained at the ideal spacing that provides maximal anchoring potential.

An alternate embodiment of anchor stylet is depicted in FIG. 4, wherein the anchoring wire holder 16 is eliminated and the anchoring wires 12 are merely attached to each other, such as at the proximal end 28 of the collective anchoring wires 12. The connection 39 securing the anchoring wires together can include a crimp or band, as shown in FIG. 4, or alternatively a solder joint, spot weld, adhesive or some other well known means of joining wires. Possible situations where the anchoring wire holder 16 might be omitted would be where reloading of the anchor stylet 40, once withdrawn, would not be necessary, and where the size and/or number of anchoring wires would not allow the extra cannula and still have a device with the desired small diameter. In the illustrative embodiment, used in brachytherapy procedures, the preferred diameter of anchoring wire 12 is 0.012"; however, larger or smaller diameter wire can be used, depending on the application. Using larger wire in the 0.010–0.014" range would reduce the likelihood of using the anchoring wire holder 16. The additional function of the wire holder cannula 16 is to provide rigidity to the anchor stylet 40. The use of smaller wire permits increasing the number of barbs 15 of the anchor stylet 40. FIG. 5 depicts an alternative embodiment having five barbs 15 (and five anchoring wires 12). Two to 9 wires represents a possible range of barbs with the preferable number being 3 to 7.

An alternative embodiment of the anchor stylet is depicted in FIG. 6 in which the anchoring wires 12 do not extend the length of the device, but rather the individual anchor wires are attached to a proximal shaft 17 by a well known method of connecting 31 such as a solder joint or crimp. The proximal shaft can be made of the same or a different material and can be made rigid or flexible.

The anchoring wires 12, preferably made of nitinol or other superelastic alloy, are formed to the desired curve shape 41 by well-known methods of either heat treating or cold working the wires until deformation occurs with bending stresses removed. In the case of the illustrative embodiment, a bend having a 0.09025" inside radius is produced by maintaining the 0.012" nitinol wire over a 0.185" pin and subjecting the wire to extreme heat. To cold work the wire, it must be overstressed over a mandril or pin until permanent deformation occurs such that partial recovery results in the desired shape. Cold working yields a bending region contains a localized region of martensitic material, whereas heat treatment produces a uniformly austenitic state in the absence of further stress being applied. Stress-induced martensite results from bending or stressing superelastic material in the austenitic state. This condition occurs while the barbs 15 are retracted into the sleeve cannula 13 or needle cannula 11.

Returning to FIG. 2, the outer needle cannula 11 delivers the anchor stylet 40 to the target site. The distal end 20 of outer needle cannula 11 of the illustrative embodiment can include a sharp beveled tip 25 to facilitate penetration of tissue. To increase visibility of the device during placement, an imaging enhancement component 19 can be included at or near the distal end 20 of the outer needle cannula. In the illustrative embodiment, the imaging enhancement component 19 comprises an echogenic region 21 having a surface specially textured to reflect energy from an ultrasound delivery source. Alternatively, imaging enhancement component 19 can include a material of increased radiopacity such as tantalum, platinum, gold, etc. to permit better visualization under fluoroscopy. This enhancement may include bands, printed indicia, or markers incorporated into the needle wall such as eyelets filled with radiopaque material. Additionally, one or more components of the anchoring device 10 itself can be made of radiopaque material.

In the illustrative embodiment, which is optimized for use as a stabilization device during a brachytherapy procedure, the outer needle cannula 11 is approximately 25 cm long and made from 18 gauge extra-thin wall stainless steel cannula; optionally the length may be approximately 20 cm. The sleeve cannula 13 is approximately 28 cm and made of 19.5 gauge thin-wall stainless steel cannula. The anchoring wire holder 16 comprises a 21.5 gauge thin-wall cannula that is approximately 29 cm in length. In the illustrative embodiment, each of the cannulae include a 2–3 cm handle portion (22,23,24) comprised of a plastic sleeve or other material attachable to the cannula. As shown in FIG. 1, handle 24 of the anchoring wire holder 16 is situated at the proximal end 28 of the device 10 with handle 23 of the sleeve cannula 13 adjacent to handle 24. When the handles 23 and 24 are abutting, the barbs are exposed from the distal end 44. Withdrawal of handle 24 about 5 mm allows the barbs to retract into the sleeve cannula 13. Handle 22 of the outer needle cannula 11 is situated adjacent to handle 23. As with handles 23 and 24, when handles 22 and 23 are abutting, the barbs 15 are exposed from the tip 20 of the needle cannula 11 and retract when handle 23 is withdrawn about 5 cm. Color coding the individual handles (22,23,24) allows the operator to easily distinguish the position of the handles and determine the deployment state from viewing the portion of the device 10 outside the patient.

The device of FIG. 1 includes a longitudinally slidable locking member 18 that allows the anchoring device to be secured or locked against a template such as that which is often used in conjunction with brachytherapy seeding or interstitial hyperthermia procedure. The slidable locking member 18 of the illustrative embodiment is an 0.3" diameter pin vise that can be positioned against the template and tightened to prevent longitudinal movement. While the proximal handle 22 of the outer needle cannula 11 prevents the pin vise 18 from being removed from the proximal end 28 of the device 10, an alternative embodiment of the invention includes cannulae (11,13,16) without proximal handles (22,23,24) such that the locking member 18 is removable from the needle cannula 11 while the device is being used in the patient. Still another embodiment includes having a longitudinal side channel on the locking device that allows it to be laterally removed from the needle cannula 11 without requiring elimination of the proximal handles (22, 23,24).

Figure 7:
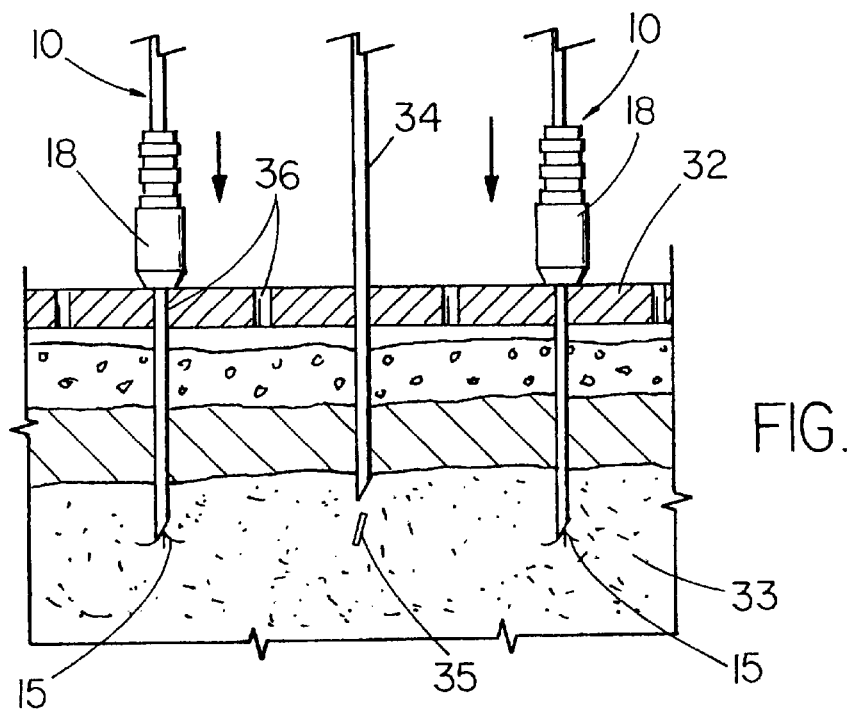
FIG. 7 depicts a conceptual view of the device of FIG. 1 being used as an anchor in a brachytherapy procedure.

FIG. 7 depicts a conceptual view of use of the device of FIG. 1 as an anchor in a brachytherapy procedure. In the illustrative example, a pair of anchoring devices 10 are inserted through holes 36 in the template 32, which is usually part of a stereotaxic guiding system attached to the patient. The second anchoring device 10 permits better stabilization of the anatomical site 33 or structure being treated. Immobilization of the structure is especially important in prostate brachytherapy where the prostate gland 33 must be maintained at a constant distance from the template 32 so that a given brachytherapy delivery device 34 can be introduced to a precise, known depth to deliver a radioactive seed 35 at the desired target location. Without proper anchoring, the prostate is prone to movement as it is being manipulated, making precise placement very difficult. Another procedure in which anchoring is important is laparoscopic cryogenic treatment of kidney tumors. Without sufficient anchoring, significant movement of the kidney is likely to occur during the procedure as the cryoprobe is advanced to the treatment site.

While the present invention is effective as an anchoring device used together with other ancillary treatment devices, a unique benefit is the ability to maintain position of the outer needle cannula 11 at the desired anatomical site while remove the anchor stylet 40 with sleeve cannula 13, then introducing another instrument to infuse/aspirate material from the site, and finally, reintroducing the anchor stylet 40 inside the needle cannula 13 if desired.

Figure 8:
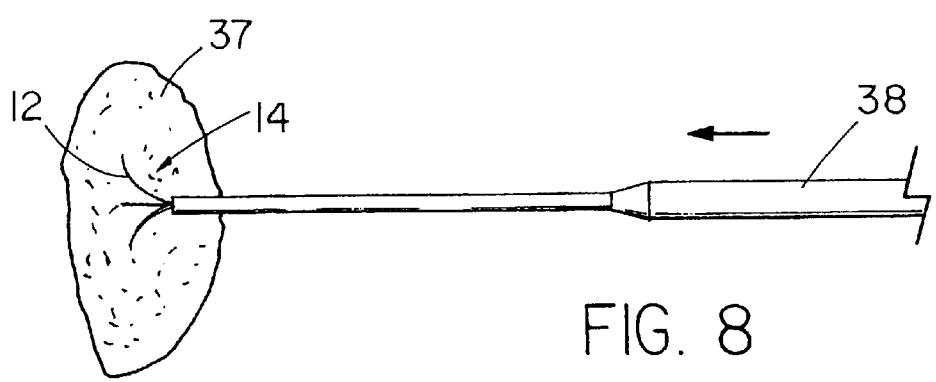
FIG. 8 depicts the device of FIG. 1 with a medical device being advanced over the anchoring stylet and sleeve cannula with the needle cannula having been removed.

An alternate use of the present device is as a guide for introducing other treatment devices 38 over the anchoring stylet 40 as depicted in FIG. 8. If proximal handles 23 and 24 are not present or sized to allow the outer needle cannula 11 to slide over the sleeve cannula 13 and anchor stylet 40, then removal of the outer needle cannula permits a dilator with sheath, catheter, or other device 38, such as a cryoprobe, electrosurgical device, etc., to be advanced over the anchor stylet 40 and sleeve cannula 13 to precisely deliver treatment to the target site. Optionally, the sleeve cannula 13 can be removed along with the needle cannula 11 with the barbs 15 then being closed by reintroducing the sleeve cannula 13 and/or the needle cannula 11 or using the ancillary device 38, if appropriate, to advance over the distal portion 14 of the anchoring wires 12 to permit removal of the anchor stylet 40.

The anchoring device functions both as a means to stabilize movement of the anatomical site, while providing a visible target under fluoroscopy or ultrasound and a conduit through which devices or materials can be introduced. It is envisaged that the present invention can be used to mark, stabilize, and treat tumor by brachytherapy, chemotherapy, cryotherapy, thermal ablation, photo radiation therapy, or other modalities. Other possible uses include gene therapy, biopsy procedures, aspiration, or infusion of other types of medicants.

What is claimed is:

1. A localization device (10) comprising:
   an outer needle cannula (11) having a distal end (20);
   a plurality of anchoring wires (12) comprising a superelastic material, the anchoring wires further having distal portions (14) extending laterally outward while in the unstressed state to form barbs (15) capable of engaging tissue; and
   a sleeve cannula (13) to constrain the distal portions of the anchoring wires into a substantially straight configuration, the sleeve cannula slidably disposed within the outer needle cannula, the distal portions of the anchoring wires extending beyond the distal end of the sleeve cannula and the distal end of the outer needle cannula in the deployed condition.

2. The device of claim 1 wherein the anchoring needles extend substantially the length of the localization device.

3. The device of claim 2 further including an anchoring wire holder (16) comprising a hollow cannula, the anchoring wires fixedly attached within the lumen of the anchoring wire holder such that each of the distal portions of the anchoring wires radiate outward therefrom in their unstressed state.

4. The device of claim 1 wherein the distal tip of the outer needle cannula includes a beveled edge.

5. The device of claim 1 wherein the anchoring needles are attached about the distal end of a proximal shaft (17), the proximal shaft extending at least substantially the length of the localization device.

6. The device of claim 1 further comprising a movable securing member (18) disposed over the outer needle cannula.

7. The device of claim 6 wherein the movable collet can be removed from the proximal end of the localization device.

8. The device of claim 1 wherein the outer needle cannula further comprises an imaging enhancement component.

9. The device of claim 8 wherein the imaging enhancement component comprises an echogenic marker.

10. The device of claim 8 wherein the imaging enhancement component comprises a radiopaque material.

11. The device of claim 1 wherein the anchoring wires comprise a nickel-titanium alloy.

12. A localization device (10) comprising:
    an outer needle cannula (11);
    a plurality of anchoring wires (12) made of a superelastic material, the distal portions (14) of the anchoring wires extending laterally outward in the unstressed state to form barbs (15) capable of engaging tissue, the anchoring needles extending substantially the length of the localization device;
    an anchoring wire holder (16) comprising a hollow cannula, the anchoring wires fixedly attached within the lumen of the anchoring wire holder such that each of the distal portions of the anchoring wires radiate outward therefrom in their unstressed state; and
    a sleeve cannula (13) to constrain the distal portions of the anchoring wires into a substantially straight configuration, the sleeve cannula slidably disposed within the outer needle cannula, the distal portions of the anchoring wires extending beyond the distal end of the sleeve cannula and the distal end of the outer needle cannula in the deployed condition.

13. The device of claim 12 further comprising a movable collet (18) disposed over the outer needle cannula.

14. The device of claim 13 wherein the movable collet can be removed from the proximal end of the localization device such that an ancillary device can be advanced thereover.

15. The device of claim 12 wherein the outer needle cannula further comprises an imaging enhancement component.

16. The device of claim 15 wherein the imaging enhancement component comprises an echogenic marker.

17. The device of claim 15 wherein the imaging enhancement component comprises a radiopaque material.

18. The device of claim 12 wherein the anchoring wires comprise a nickel-titanium alloy.

19. A localization device (10) comprising:
    an outer needle cannula (11) having a distal end (20), the outer needle cannula having a echogenic region disposed about the distal end thereof;
    at least three anchoring wires (12) comprising a nickel-titanium alloy, the distal portions (14) of the anchoring wires extending laterally outward in the unstressed state to form barbs (15) capable of engaging tissue;
    an anchoring wire holder (16) comprising a hollow cannula, the anchoring wires fixedly attached within the lumen of the anchoring wire holder such that each of the distal portions of the anchoring wires radiate outward therefrom in their unstressed state;

a sleeve cannula (13) to constrain the distal portions of the anchoring wires into a substantially straight configuration, the sleeve cannula slidably disposed within the outer needle cannula, the distal portions of the anchoring wires extending beyond the distal end of the sleeve cannula and the distal end of the outer needle cannula in the deployed condition; and a movable collet slidably disposed over the outer needle cannula, the collet capable of being removed from the proximal end of the localization device.

* * * * *